United States Patent
New et al.

(10) Patent No.: US 6,258,377 B1
(45) Date of Patent: *Jul. 10, 2001

(54) HYDROPHOBIC PREPARATIONS CONTAINING MEDIUM CHAIN MONOGLYCERIDES

(75) Inventors: Roger Randal Charles New, London; Christopher John Kirby, Berkshire, both of (GB)

(73) Assignee: Provalis UK Limited (GB)

(*) Notice: Subject to any disclaimer, the term of this patent is extended or adjusted under 35 U.S.C. 154(b) by 7 days.

This patent is subject to a terminal disclaimer.

(21) Appl. No.: 09/218,289

(22) Filed: Dec. 22, 1998

Related U.S. Application Data

(63) Continuation of application No. PCT/GB97/01775, filed on Jul. 2, 1997.

(30) Foreign Application Priority Data

Jul. 2, 1996 (GB) .................................................. 9613858

(51) Int. Cl.$^7$ ...................................................... A61K 9/127
(52) U.S. Cl. ............................. 424/450; 424/400; 514/2; 514/21; 514/937; 514/943
(58) Field of Search .................................... 424/400, 450; 514/2, 21, 937–943

(56) References Cited

U.S. PATENT DOCUMENTS 4,156,719 * 5/1979 Sezaki ................................ 424/118

FOREIGN PATENT DOCUMENTS

| | | |
|---|---|---|
| 020796 | 3/1988 | (EP) . |
| WO93/02664 | 2/1993 | (WO) . |
| WO94/08603 | 4/1994 | (WO) . |
| WO94/08605 | 4/1994 | (WO) . |
| WO94/12154 | 6/1994 | (WO) . |
| WO94/19003 | 9/1994 | (WO) . |
| WO 95/13795 | 5/1995 | (WO) . |
| WO96/14871 | 5/1996 | (WO) . |
| WO 96/17593 | 6/1996 | (WO) . |
| WO 96/17594 | 6/1996 | (WO) . |
| WO 97/34581 | 9/1997 | (WO) . |

OTHER PUBLICATIONS

Constantinides et al., Formulation and Intestinal Absorption Enhancement Evaluation of Water–in–Oil Microemulsions Incorporating Medium–Chain Glycerides, Pharmaceutical Research, vol. 11, No. 10 pp. 1385–1390 (1994).

Higaki, et al., Effect of Medium–Chain Glycerides (MGK®) on the Intestinal Absorption and the Hepatobiliary Transport of Bromthymol Blue, J. Pharmacobio–Dyn, 9, 532–539 (1986).

Sekine, et al., Improvement of Bioavailability of Poorly Absorbed Drugs. I. Effect of Medium Chain Glyceride Base on the Rectal Absorption of Cefmetazole Sodium in Rats, J. Pharm.Dyn., 7, 856–863 (1984).

Unowsky, et al., Effect of Medium Chain Glycerides on Enteral and Rectal Absorption of β–Lactam and Aminoglycoside Antibiotics, Chemotherapy 34:272–276 (1988).

Watanabe, et al., Absorption Enhancement of Rectally Infused Cefoxitin by Medium Chain Monoglycerides in Conscious Rats, Journal of Pharmaceutical Sciences, vol. 77, No. 10, pp. 847–849, (1988).

* cited by examiner

*Primary Examiner*—Gollamudi S. Kishore
(74) *Attorney, Agent, or Firm*—Pennie & Edmonds LL

(57) ABSTRACT

Hydrophobic preparations which are useful as, among other things, pharmaceutical delivery systems comprise: (i) an oil phase comprising one or more medium chain monoglycerides, such as Akoline MCM™; (ii) at least one amphiphile, preferably including a phospholipid such as phosphatidyl choline; and (iii) a hydrophilic species, which may be a protein such as insulin or calcitonin or another macromolecule, solubilized or otherwise dispersed in the one or more glycerides. The hydrophilic species is one that is not normally soluble in the glycerides.

9 Claims, No Drawings

HYDROPHOBIC PREPARATIONS CONTAINING MEDIUM CHAIN MONOGLYCERIDES

This application is a continuation of International Application PCT/GB97/01775 filed Jul. 2, 1997.

The present invention relates to preparations of substances in hydrophobic solvents in which they would normally be soluble and to processes for obtaining these preparations. In particular, the invention relates to preparations of hydrophilic species in mixtures of medium chain monoglycerides (MCMs) and diglycerides.

The invention in particular applies to hydrophilic macromolecules which would not normally be soluble in oils or other hydrophobic solvents.

For many applications, e.g. in the pharmaceutical sciences, in food technology or the cosmetics industry, work with proteins and similar macromolecules presents problems because their hydrophilicity and high degree of polarity limit the extent to which they can interact with or incorporate into lipid phases. Many natural systems employ lipidic barriers (eg skin, cell membranes) to prevent access of hydrophilic molecules to internal compartments; the ability to disperse proteins in lipidic vehicles would open up a new route to introduction of these macromolecules into biological systems, whereby the lipid medium containing the protein can integrate with the hydrophobic constituents of barriers, instead of being excluded by them.

We have previously disclosed, in WO-A-9513795, WO-A-9617593 and WO-A-9617594, methods for preparing hydrophobic preparations where a hydrophilic species is solubilised in a hydrophobic phase in which it would not normally be soluble. In particular, these methods are suitable for solubilising proteins.

Although the above-described preparations provide simple and efficient methods for solubilising macomolecules such as proteins, we have now found that the macromolecule delivery properties of the preparations can be improved by the use of a particular oil phase and, optionally, particular amphiphiles. This is particularly advantageous when the macromolecule to be solubilised is a protein, eg a pharmaceutically active protein, since the preparations disclosed herein provide not only enhanced uptake of the therapeutic macromolecule but also good dose repeatability.

Thus, in a first aspect, the present invention provides a hydrophobic preparation comprising:
(i) an oil phase comprising one or more medium chain monoglycerides; and
(ii) at least one amphiphile;
(iii) a hydrophilic species solubilised or otherwise dispersed in the mixture of glycerides;
wherein the hydrophilic species is one that is not normally soluble in the one or more monoglycerides.

In the context of the present invention "hydrophobic preparation" is a preparation in which the hydrophilic species is not present in aqueous phase. Such a hydrophobic preparation is particularly suitable for use in orally delivering a hydrophilic macromolecule such as a protein.

The prior art does contain a number of examples of the use of medium chain monoglycerides as permeation enhancers in the intestine (Sekine et al, *J.Pharmacobiodyn.*, 7:856–63 (1984); Higkai et al, *J.Pharmacobiodyn.*, 9:532–9 (1986); Unowsky et al, Chemotherapy, 34:272–6 (1988); Watanabe et al, *J.Pharm.Sci.*, 77:847–9 (1988); Yeh et al, *Pharm.Res.*, 11:1148–54 (1994); Constinides et al, *Pharm.Res.*, 11:1385–90 (1994)). However, in every case the formulations disclosed are ones where the active principle/drug is solubilised in an aqueous phase. In fact until the methods disclosed in, inter alia, WO-A-9513795 preparations where a hydrophilic species was truly and readily solubilised in a hydrophobic phase, with retention of biological activity, were not available.

Preparations in accordance with the invention will generally have no bulk aqueous phase and may have no free water molecules.

In a preferred embodiment the oil phase i) will compose a mixture of medium chain mono- and diglycerides. Suitably, medium chain glycerides useful in the present invention have chain lengths of 8 to 10 carbon atoms, for example, they can comprise straight chain saturated fatty acids. In another embodiment the oil phase i) may comprise one or more medium chain monoglycerides together with at least one other component such as oleic acid, glycerol mono-oleate or gelucides. For both these embodiments the essential component will be the medium chain monoglyceride(s). Whether medium chain monoglyceride(s) are used alone or as mixtures of glycerides or the like, the oil component used should be such that the amount of monoglyceride(s) present should be maximised while ensuring that the oil component remains liquid at a temperature of 45° C. or lower. In particular, monoglyceride(s) can make up 40–90% of the total amount of oil present, preferably 60–70%. An example of a suitable mixture of glycerides is Akoline MCM™ which contains both medium chain mono- and diglycerides, available from Karlshamns Sweden AB, S/374 82 Karlsbamn, Sweden.

Preferably, the ratio of amphiphile:macromolecule is in the range 1:1 to 20:1 by weight and more preferably in the range 2:1 to 8:1 by weight.

Examples of suitable amphiphiles include phospholipids such as phosphatidyl choline, phosphatidic acid, phosphatidyl glycerol, phosphatidyl ethanolamine and lyso-derivatives of these, octyl glucoside and other glycolipids, tocopherol succinate and cholesterol hemisuccinate. Other suitable amphiphiles include phosphatidyl serine, sodium docusate and hydroxypropyl cellulose. More than one amphiphile may be used.

In one preferred embodiment the amphiphile used is a bile salt. In the present invention it should be understood that the terms bile salt and bile acid are used interchangeably because whether the salt or its conjugate acid is present will depend on the pH of the surrounding environment.

Bile salts are naturally occurring surfactants. They are a group of compounds with a common "backbone" structure based on cholanic acid found in all mammals and higher vegetables. Bile salts may be mono-, di- or tri-hydroxylated; they always contain a 3α-hydroxyl group whereas the other hydroxyl groups, most commonly found at $C_6$, $C_7$ or $C_{12}$, may be positioned either above (β) or below (α) the plane of the molecule.

Within the class of compounds described as bile salts are included amphiphilic polyhydric sterols bearing carboxyl groups as part of the primary side chain. The most common examples of these in mammals result from cholesterol metabolism and are found in the bile and, in derivatised form, throughout the intestine.

In the context of this specification, the term may also apply to synthetic analogues of naturally occurring bile salts which display similar biological effects, or to microbially derived molecules such as fusidic acid and its derivatives.

The bile salt (or salts) may be either unconjugated or conjugated. The term "unconjugated" refers to a bile salt in which the primary side chain has a single carboxyl group which is at the terminal position and which is unsubstituted.

Examples of unconjugated bile salts include cholate, ursodeoxycholate, chenodeoxycholate and deoxycholate. A conjugated bile salt is one in which the primary side chain has a carboxyl group which is substituted. Often the substituent will be an amino acid derivative which is inked via its nitrogen atom to the carboxyl group of the bile salt. Examples of conjugated bile salts include taurocholate, glycocholate, taurodeoxycholate and glycodeoxycholate.

Thus, in the present invention examples of suitable bile salts include cholate, deoxycholate, chenodeoxycholate and ursodeoxycholate, with ursodeoxycholate being particularly preferred. Other bile salts which may be employed include taurocholate, taurodeoxycholate, taurouodeoxycholate, taurochenodeoxycholate, glycholate, glycodeoxycholate, glycoursodeoxycholate, glycochenodeoxycholate, lithocholate, taurolithocholate and, glycolithocholate.

In the present invention the term "hydrophilic species" relates to any species which is generally soluble in aqueous solvents but insoluble in hydrophobic solvents. The range of hydrophilic species of use in the present invention is diverse but hydrophilic macromolecules represent an example of a species which may be used.

A wide variety of macromolecules is suitable for use in the present invention. In general, the macromolecular compound will be hydrophilic or will at least have hydrophilic regions since there is usually little difficulty in solubilising a hydrophobic macromolecule in oily solutions. Examples of suitable macromolecules include proteins and glycoproteins, oligo and polynucleic acids, for example DNA, eg plasmid DNA, and RNA, as well as DNA and/or RNA analogues, polysaccharides such as heparin (particularly low molecular weight heparin) and supramolecular assemblies of any of these including, in some cases, whole cells or organelles. It may also be convenient to co-solubilise a small molecule such as a vitamin in association with a macromolecule, particularly a polysaccharide such as a cyclodextrin. Small molecules such as vitamin B12 may also be chemically conjugated with macromolecules and may thus be included in the compositions.

Examples of particular proteins which may be successfully solubilised by the method of the present invention include insulin, calcitonin, haemoglobin, cytochrome C, horseradish peroxidase, aprotinin, mushroom tyrosinase, erythropoietin, somatotropin, growth hormone, growth hormone releasing factor, galanin, urokinase, Factor IX, tissue plasminogen activator, superoxide dismutase, catalase, peroxidase, ferritin, interferon, Factor VIII and fragments thereof (all of the above proteins can be from any suitable source). Other proteins include soy bean trypsin inhibitor, GLP1, other blood coagulation factors, somatostatin, hirudin, and LHRH and analogues and fragments of all of them.

Mixtures of one or more of these or other proteins may be solubilised by the invention.

It seems that there is no upper limit of molecular weight for the macromolecular compound since dextran having a molecular weight of about 1,000,000 can easily be solubilised by the process of the present invention.

In addition to macromolecules, the process of the present invention is of use in solubilising smaller organic molecules as well as or instead of macromolecules. Examples of small organic molecules include glucose, carboxyfluorescin and many pharmaceutical agents, for example anticancer agents, but, of course, the process could equally be applied to other small organic molecules, for example vitamins or pharmaceutically or biologically active agents. In addition, compounds such as calcium chloride and so phosphate can also be solubilised using this process. Indeed, the present invention would be particularly advantageous for pharmaceutically and biologically active agents since the use of non aqueous solutions may enable the route by which the molecule enters the body to be varied, for example to increase bioavailability.

Small organic molecules which may be incorporated into macromolecule-containing preparations of the invention include stabilising agents such as polyglycerols, PEGs and glycerol (particularly in the case of insulin or, possibly, other proteins), chelating agents, such as citric acid, EDTA and EGTA, and antioxidants such as ascorbate.

Another type of species which may be included in the hydrophobic compositions of the invention is an inorganic material such as a small inorganic molecule or a colloidal substance, for example a colloidal metal. The process of the present invention enables some of the pries of a colloidal metal such as colloidal gold, palladium, platinum or rhodium, to be retained even in hydrophobic solvents in which the particles would, under normal circumstances, aggregate. This could be particularly useful for catalysis of reactions carried out in organic solvents.

The hydrophobic preparations of the invention may also optionally comprise further components. Examples of these include antioxidant, metal chelating agents, buffering agents and dispersion agents. Examples of suitable dispersion agents include surface active agents such as the Tween, Span and Brij classes of agent, as well as polyoxyethylated castor oil derivatives, and other POE-containing surfactants.

The hydrophobic preparations of the present invention can be prepared using a method comprising:

(i) associating the hydrophilic species with the amphiphile in a liquid medium such that, in the liquid medium, there is no chemical interaction between the amphiphile and the hydrophilic species;

(ii) removing the liquid medium to leave an array of amphiphile molecules with their hydrophilic bead groups orientated towards the hydrophilic species; and (iii) providing a mixture of medium chain mono- and diglycerides around the hydrophilic species/amphiphile array.

Such methods are disclosed in WO-A-9513795. In particular, the hydrophobic preparations of the present invention can be prepared by methods disclosed in PCT patent application No. PCT/GB97/00749 which comprise:

(i) associating the hydrophilic species with the amphiphile in the presence of a hydrophobic phase; and (ii) removing any hydrophilic solvent which is present; wherein the hydrophilic solvent removal step is carried out under conditions which maintain the hydrophobic phase in a solid state.

Preferably, when using this method, the hydrophilic species and the amphiphile are first dissolved in a hydrophilic solvent, eg an aqueous solvent, often water alone, and this solution is then brought into association with the glyceride mixture. The hydrophilic solvent removal step is conveniently achieved by lyophilisation, such that it is carried out at temperatures which will ensure that the glyceride mixture is maintained in the solid state until all the water has been removed. Under certain circumstances, the oil may become liquid during lyophilisation, as a result of local rises in temperature in parts of the solid block (usually at the surface and edges) where all the hydrophilic solvent has already been removed. Here the cooling effect deriving from sublimation of hydrophilic solvent no longer exists, and in those areas the oil will melt. This situation will lead to the production of a satisfactory end-product providing that the oil is allowed to drain away from the remainder of the solid block as soon as it appears (if not, then accumulating oil will form a layer which prevents further removal of hydrophilic solvent).

Alternatively, the temperature during lyophilisation can be maintained such that the oil remains solid even after the hydrophilic solvent has been driven off. In this case following lyophilisation, the temperature of the preparation is elevated to produce the single phase preparation. This can often simply be achieved by bringing the lyophilised preparation up to room temperature which in turn will cause the glyceride mixture to return to the liquid state. Other methods for removal of hydrophilic solvent may also be employed, eg spray drying.

The hydrophobic preparation of the present invention are extremely versatile and have many applications. They may either be used alone or they may be combined with an aqueous phase to form an emulsion or similar two phase composition which forms a second aspect of the invention.

In this aspect of the invention there is provided a two phase composition comprising a hydrophilic phase and a hydrophobic phase, the hydrophobic phase comprising a hydrophobic preparation of the invention which is obtainable by the methods described above.

Generally, in this type of composition, the hydrophobic phase will be dispersed in the hydrophilic phase.

As mentioned herein the hydrophobic preparations of the invention have particular advantages in that the hydrophilic species is readily taken up, eg into the bloodstream following oral administration. They are therefore particularly suitable for the oral delivery of protein for example. However, the skilled man will appreciate that the preparations of the invention will also provide advantages for other routes of administration, eg topical or vaginal. This, in a third aspect the present invention provides a pharmaceutical formulation comprising a hydrophobic preparation of the invention. Pharmaceutical formulations within the scope of the invention include capsules, tablets and other presentations. In addition, in a fourth aspect the present invention provides the use of a hydrophobic preparation of the invention in the preparation of a medicament for oral delivery of a hydrophilic species, for instance a hydrophilic macromolecule such as a protein. The invention can also be used to modify the immune response, whereby stimulation or suppression.

Preferred features of each aspect of the invention are equally applicable to each other aspect *mutatis mutandis*.

The invention will now be described with reference to the following examples which should not be construed as in any way limiting the invention.

EXAMPLE 1

Preparation of Formulation Containing Calcitonin/ PC Complex (i) Preparation of Phospholipid Dispersion 1 Weigh out 1.6 g of SOYA PHOSPHATIDYL CHOLINE in a boiling tube with a ground glass stopper and add DISTILLED WATER to give a final weight of 8 g. Flush with nitrogen, stopper well and seal with parafilm and mix gently on orbital shaker until all the solid has dispersed.

2 Transfer to a glass round-bottomed sonicator vessel.

3 Clamp the sonicator vessel into the Sonics 4 Materials Vibra Cell VC X 600 Sonicator fitted with a 1 inch diameter probe and immerse the probe until its base is sufficiently below the meniscus of the liquid. Use a strip of cling film to form a sleeve between the probe and the top of the tube and purge the air space above the liquid with nitrogen. Immerse the sonicator vessel in an ice slurry bath.

4 Sonicate the lipid pension at an amplitude of 50%, in 1 second bursts interspersed with 4 second cooling intervals, until an opalescent dispersion is formed (normally 4 minutes total sonication time).

5 Transfer the dispersion to a plastic conical centrifuge tube and centrifuge for 15 minutes at 1200 g. Separate the supernatant from any pellet that is present.

6 Dilute two-fold in distilled water to give a final concentration of 100 mg/ml of phospholipid.

(ii) Peparation of Protein Solution

7 Weigh out 20 mg of APROTININ in a 2 ml glass screw-capped vial and add 1 ml of DISTILLED WATER. Screw cap tightly and mix gently until all the solid is dissolved.

8 Weigh out 16 mg of SALMON CALCITONIN in a ml glass screw-capped vial and add 0.8 ml of DISTILLED WATER. Screw cap tightly and mix gently until all the solid is dissolved.

9 Weigh out 50 mg of ASCORBIC ACID and 5 mg of CITRIC ACID in a ml glass screw-capped vial and add 1 ml of DISTILLED WATER. Screw cap tightly and mix gently until all the solid is dissolved.

10 To each of three glass screw-capped 10 ml vials dispense 2 ml of phospholipid dispersion (200 mg solid) from step 6, 250 µl of aprotinin solution (5 mg of solid) from step 7, 250 µl of calcitonin solution (5 mg of solid) from step 8, and 200 µl of ascorbic acid/citric acid solution (10 mg and 1 mg of solid respectively) from step 9 Mix contents of each vial gently.

(iii) Lyophilisation of Aqueous Phase

11 Freeze the content of each vial rapidly in liquid nitrogen.

12 Lyophiise overnight at a condenser temperature of less than −40° C. and a vacuum of less than 0.1 mBar.

(iv) Preparation of Oil Phase

13 Weigh out 0.8 g of POLYSORBATE 80 and 7.2 g of AKOLINE MCM into a B8 glass screw-capped vial. Flush vial with nitrogen, screw cap tightly and seal with parafilm and mix gently on roller mixer until a homogenous solution has been obtained.

(v) Solubilisation in Oil Phase

14 After samples have dried down fully in the lyophiliser, add to each vial 1.779 g of oil phase from step 14. Flush each vial with nitrogen, screw caps tightly and seal with parafilm.

15 Allow solids to dissolve by mixing on roller mixer at room temperature for two hours, followed by shaking at 37° C. until a clear solution has formed.

16 Store at +4° C. until required for use.

(vi) Administration in vivo

17 Warm each vial to 37° C. in a water bath in order to melt the oil and form a clear solution.

18 To each vial add 4 ml of warm PBS, vortex for 30 seconds and administer 1.2 ml to one pig ij. as described above.

EXAMPLE 2

Preparation of Formulation Containing Insulin/ Chenodeoxycholate Complex (i) Preparation of Chenodeoxycholate Solution 1 Weigh out 6.0 g of SODIUM CHENO DEOXY CHOLATE in a glass conical flask and add DISTILLED WATER to give a final weight of 60 g. Flush with nitrogen, stopper well and seal with parafilm and mix gently on orbital shaker until all the solid has dissolved.

(ii) Preparation of Protein Solution

2 Weigh out 120 mg of APROTININ in a 2 ml glass screw-capped vial and add 6.0 ml of DISTILLED WATER. Screw cap tightly and mix gently until all the solid is dissolved.

3 Weigh out three separate lots of 106.5 mg of INSULIN into (A) a 100 ml conical flask, (B) a 25 ml conical flask and (C) a 10 ml glass screw-capped vials. To flask (A) add 30 ml of chenodeoxycholate solution (3 g solid) from step 3.1.1. To flask (B) add 15 ml of chenodeoxycholate solution (1.5 g solid), and to vial (C) add 7.5 ml (0.75 g solid). Cover flasks and vial with parafilm and mix gently on orbital shaker at 37° C. until all the solid is dissolved.

4 Weigh out 54 mg of CITRIC ACID in a 2 ml glass screw-capped vial and add 6.0 ml of DISTILLED WATER. Screw cap tighly and mix gently until all the solid is dissolved.

5 To each of twelve glass screw-capped 7 ml vials dispense 2 ml of insulin/chenodeoxycholate solution (A) from step 3, 100 µl of aprotinin solution from step 2, and 100 µl of citric acid solution from step 4. Mix contents of each vial gently.

6 To each of twelve glass screw-capped 7 ml vials dispense 1 ml of insulin/chenodeoxycholate solution (B) from step 3, 100 µl of aprotinin solution from step 2, and 100 µl of citric acid solution from step 4. Mix contents of each vial gently.

7 To each of twelve glass screw-capped 7 ml vials dispense 1.5 ml of insulin/chenodeoxycholate solution (C) from step 3, 100 µl of aprotinin solution from step 2, and 100 µl of citric acid solution from step 4. Mix contents of each vial gently.

(iii) Lyophilisation of Aqueous Phase

8 Freeze the contents of each vial rapidly in liquid nitrogen and lyophilise overnight at a condenser temperature of less than −40° C. and a vacuum of less than 0.1 mBar.

(iv) Preparation of Oil Phase

9 Weigh out 6.0 g of POLYSORBATE 80 and 54 g of AKOLINE MCM into a 100 ml glass bottle. Flush vial with nitrogen, screw cap tightly, seal with parafilm and mix gently on roller mixer until a homogenous solution has been obtained.

(v) Solubilisation in Oleic Add

10 After samples have dried down fully in the lyophiliser, add to each vial of preparation (A) 0.79 g of oil phase from step 10. Flush each vial with nitrogen, screw caps tightly and seal with parafilm.

11 After samples have dried down fully in the lyophiliser, add to each vial of preparation (B) 0.89 g of oil phase from step 10. Flush each vial with nitrogen, screw caps tightly and seal with parafilm.

12 After samples have dried down fully in the lyophiliser, add to each vial of preparation (C) 0.94 g of oil phase from step 10. Flush each vial with nitrogen, screw caps tightly and seal with parafilm.

13 Allow solids to dissolve by mixing on roller mixer at room temperature for two hours, followed by shaking at 37° C. until a clear solution has formed and store at +4° C. until required for use.

(vi) Administration in vivo

14 Warm each vial to 37° C. in a water bath in order to melt the oil and form a clear solution.

15 To each vial add 2 ml of warm PBS, vortex for 30 seconds and administer the contents of one whole vial to one pig i.j. as described above.

EXAMPLE 3

Preparation of Formulation Containing Insulin/PC Complex (i) Preparation of Phosphdipid Dispersion 1 Weigh out 2 g of SOYA PHOSPHATIDYL CHOLINE in a boiling tube with a ground glass stopper and add DISTILLED WATER to give a final weight of 8 g. Flush with nitrogen, stopper well and seal with parafilm and mix gently on orbital shaker until all the solid has dispersed.

2 Transfer to a glass round-bottomed sonicator vessel.

3 Clamp the sonicator vessel into the Sonics 4 Materials VibraCell VCx60 ultrasonicator fitted with a 1 inch diameter and immerse the probe until its base is 1 cm below the meniscus of the liquid. Use a strip of cling film to form a sleeve between the probe and the top of the tube and purge the air space above the liquid with nitrogen. Immerse the sonicator vessel in an ice slurry bath.

4 Sonicate the lipid suspension at an amplitude of 50%, in 1 second bursts interspersed with 4 second cooling intervals, until an opalescent dispersion is formed (normally 4 minutes total sonication time).

5 Transfer the dispersion to a plastic conical centrifuge tube and centrifuge for 15 minutes at 1200 g. Separate the supernatant from any pellet that is present.

(ii) Preparation of Protein Solution

6 Weigh out 30 mg of APROTININ in a 2 ml glass screw-capped vial and add 1.5 ml of DISTILLED WATER. Screw cap tightly and mix gently until all the solid is dissolved.

7 Weigh out 110 mg of INSULIN into a 25 ml conical flask and add all 15 ml of DISTILLED WATER to which 150 µl of GLACIAL ACETIC ACID has been added. Cover the flask with parafilm and mix gently on orbital shaker at 37° C. until all the solid is dissolved.

8 Weigh out 10 mg of SODIUM CITRATE in a 2 ml glasss screw-capped vial and add 1.5 ml of DISTILLED WATER. Screw cap tightly and mix gently until all the solid is dissolved.

9 To each of twelve glass screw-capped 7 ml vials dispense 1 ml of insulin solution (7.33 mg solid, 200 iu) from step 7, 100 µl of sodium citrate (0.67 mg solid) from step 8, 100 µl of aprotinin solution (2 mg solid) from step 6 and 400 µl of phospholipid dispersion (100 mg solid) from step 5. Mix contents of each vial gently.

(iii) Preparation of Oil Phase

10 Weigh out 1.5 g of POLYSORBATE 80 and 13.5 g of AKOLINE MCM into a 20 ml glass bottle. Flush vial with nitrogen, screw cap tightly and seal with parafilm and mix gently on roller mixer until a homogenous solution has been obtained.

(iv) Lyophilisation of Aqueous Phase

11 To each vial in step 9 add 1 ml of akoline/polysorbate 80 mixture from step 10 using a large volume positive displacement dispenser.

12 Vortex each vial rapidly for ten seconds, and then freeze immediately in liquid nitrogen.

13 Lyophilise for two nights at a condenser temperature of less than −40° C. and a vacuum of less than 0.1 mBar.

(v) Preparation of Solution in Oil

14 Remove each of the vials from the lyophiliser, flush with nitrogen, cap tightly and seal with parafilm. Incubate with gentle shaking at 37° C. until a clear solution is obtained and store at +4° C. until required for use.

(vi) Administration in vivo

15 Warm each vial to 37° C. in a water bath in order to melt the oil and form a clear solution.

16 To each vial add 2 ml of warm PBS, vortex for 30 seconds and administer the contents of one whole vial to one pig ij. as described above.

EXAMPLE 4

Preparation of Formulation Containing Insulin/
Ursodeoxyholate Complex (i) Preparation of Urso Deoxycholate Solution 1 Weigh out 525 mg of SODIUM URSO DEOXY CHOLATE in a glass conical flask and add DISTILLED WATER to give a final weight of 15 g. Flush with nitrogen, stopper well and seal with parafilm and mix gently on orbital shaker until all the solid has dissolved.

(ii) Preparation of Protein Solution

2 Weigh out 30 mg of APROTININ in a 2 ml glass screw-capped vial and add 1.5 ml of DISTILLED WATER. Screw cap tightly and mix gently until all the solid is dissolved.

3 Weigh out 110 mg of INSULIN into a 25 ml conical flask and add all 15 ml of ursodeoxycholate solution (525 g solid) from step 1. Cover the flask with parafilm and mix gently on orbital shaker at 37° C. until all the solid is dissolved.

4 Weigh out 13.5 mg of SODIUM CITRATE in a 2 ml glass screw-capped vial and add 1.5 ml of DISTILLED WATER. Screw cap tightly and mix gently until all the solid is dissolved.

5 To each of twelve glass screw-capped 7 ml vials dispense 1 ml of insulin/chenodeoxycholate solution (7.3 mg insulin/ 35 mg bile salt) from step 3, 100 $\mu$l of sodium citrate (0.9 mg solid) from step 4, and 100 $\mu$l of aprotinin solution (2 mg solid) from step 2. Mix contents of each vial gently.

(iii) Preparation of Oil Phase

6 Weigh out 1.5 g of POLYSORBATE 80 and 13.5 g of AKOLINE MCM into a 20 ml glass bottle. Flush vial with nitrogen, screw cap tightly and seal with parafilm and mix gently on roller mixer until a homogenous solution has been obtained.

(iv) Lyophilisation of Aqueous Phase

7 To each vial in step 5 add 1 ml of akoline/polysorbate 80 mixture from step 6 using a large volume positive displacement dispenser.

8 Vortex each vial rapidly for ten seconds, and then freeze immediately in liquid nitrogen.

9 Lyophilise for two nights at a condenser temperature of less than –40° C. and a vacuum of less than 0.1 mBar.

(v) Preparation of Solution in Oil

10 Remove each of the vials from the lyophiliser, flush with nitrogen, cap tightly and seal with parafilm. Incubate for ten minutes at 37° C. until a clear solution is obtained.

11 Store at +4° C. until required for use.

(vi) Administration in vivo

12 Warm each vial to 37° C. in a water bath in order to melt the oil and form a clear solution.

13 To each vial add 2 ml of warm PBS, vortex for 30 seconds and administer the contents of one whole vial to one pig ij. as described above.

EXAMPLE 5

Formulations for Intestinal Delivery of Calcitonin

Formulations were prepared as follows:

1) Mixture of Salmon Calcitonin with Akoline MCM.

As in Example 1, except that (a) the phospholipid dispersion was omitted (b) the protein-containing lyophiate was not dissolved in oil phase, (c) prior to administration to animals the protein lyophilate was dissolved in 4 ml phosphate-buffered saline and (d) the resulting solution was added to 2 ml of the oil phase (Akoline MCM/Tween 80) and dispersed by vortexing.

2) Mixture of Salmon Calcitonin with Glycerol Di-Oleate

As for formulation (1) except that glycerol di-oleate was employed in place of Akoline MCM.

3) Mixture Salmon Calcitonin with Oleic Acid.

As for formulation (1) except that oleic acid was employed in phase of Akoline MCM.

4) Oil Containing Salmon Calcitonin/PC complex in Akoline MCM.

As described in example 1.

5) Oil Containing Salmon Calcitonin/Chenodeoxycholate complex in Akoline MCM.

Formulation identical in composition to that in formulation (4) of this Example, except that sodium chenodeoxycholate was employed instead of PC at a concentration of 100 mg/g in the oil phase.

6) Oil Containing Salmon Calcitonin/Chenodeoxycholate complex in Akoline MCM.

Formulation identical in composition to that in fomulation (4) of this Example, except that aprotinin was omitted, and sodium chenodeoxycholate was employed instead of PC at a concentration of 17.5 mg/g in the oil phase.

7) Oil Containing Salmon Calcitonin/Urodeoxycholate complex in Akoline MCM.

Formulation identical composition to that in (4) above, except that aprotinin was omitted, and sodium urodeoxycholate was employed instead of PC at a concentration of 17.5 mg/g in the oil phase.

8) Oil Containing Salmon Calcitonin/Tocopherol succinate complex in Akoline

Formulation identical in composition to that in (4) above, except that aprotinin was omitted, and alpha-tocopherol succinate was employed instead of PC at a concentration of 25 mg/g in the oil phase.

9) Oil Containing Salmon Calcitonin/Tocopherol succinate complex in Akoline MCM

Formulation identical in composition to that in (4) above, except that aprotinin was omitted, and sodium docusate was employed instead of PC at a concentration of 25 mg/g in the oil phase.

EXAMPLE 6

Formulations for Intestinal Delivery of Insulin

Formulations were prepared as follows:

10) Mixture of Insulin with Akoline MCM.

As for formulation (1) except that 7.3 mg of insulin (200 iu), 2 mg of aprotinin, and 1 ml of Akoline 80 oil phase employed.

11) Oil Containing Insulin/PC Complex in Akoline MCM.

As in Example 2.

12) Oil Containing Insulin/Chenodeoxycholate Complex in Akoline MCM at High Bile Salt Concentration.

As in Example 3.

13) Oil Containing Insulin/Chenodeoxychlolate Complex in Akoline MCM at Medium Salt Concentration.

As in Example 3.

14) Oil Containing Insulin/Chenodeoxycholate Complex in Akoline MCM at Low Bile Salt Concentration.

As in Example 3.

15) Oil Containing Insulin/Urodeoxycholate Complex in Akoline MCM (with aprotinin).

As in Example 4.

16) Oil Containing Insulin/Urodeoxycholate complex in Akoline MCM (without aprotinin).

Exactly as in Example 4 except that aprotinin omitted from the preparation.

17) Solution of Insuln/Urso in Phosphate-Buffered Saline.

Lyophilised solution of insulin prepared as in step (3) of Example 4. Redissolved in Phospate-Buffered Saline (7.3 mg insulin/2 ml) before administration.

EXAMPLE 7

Animal Studies

Preparation of Animal Model

The animal model employed for testing oral formulations of calcitonin is the juvenile pig. The pig is selected because it has similar weight to man and the structure, function and size of the small intestine are similar to the human small intestine. In order to eliminate concerns relating to differences between human and porcine stomachs, the animals were surgically manipulated so that material could be introduced directly into the jejunum via an in-dwelling cannula. This also reduces the uncertainty usually associated with oral administration as to time of arrival of the dose in the intestine, and leads to improvement in the quantity of the statistics obtained.

At least 10 days before the first dosing, a fine plastic cannula was surgically inserted into the jejunum of the pig and then brought out under the skin onto the back of the pig so that the test materials can be injected into the jejunum without distressing the animal. An indwelling catheter which was also brought out through the back skin was inserted into the aorta via the medium saphenous artery so that repeated blood samples could be obtained. A second catheter was also introduced in a carotid artery.

Administration of Formulations

Pigs were tested while fully conscious in the fasting state and peptide formulations were administered via the oral route after three baseline blood samples were taken. A single experiment usually occupied a period of 8 to 9 hours and the surgically-prepared pigs participated in tests up to three times per week over a four week period. On completion of the tests the pigs were killed and the intestines examined for macroscopic and microscopic changes.

During the study water was provided ad lib and the pigs fed at 8:00 and 15:30. Any is food remaining after the 15:30 feed was removed at 16:30. On the days of treatment, the 08:00 food was withheld and ¾ of the total daily requirement was given after the last blood sample was taken.

On the days of treatment, the dosing solutions were given by installation via the in-dwelling cannula into the jejunum. The cannula was flushed through before dosing with 1 ml warm (25–30° C.) sterile phosphate-buffered saline, and flushed through after dosing with 5 ml of the same material at the same temperature. Calcitonin incorporated in the ipidic delivery system was given as a dispersion in which 2 ml of oil was vortexed in 4 ml of warm phosphate buffered saline, and 1.3 ml of the resultant dispersion was administered to each animal. Each animal received 5000 iu of calcitonin. Insulin formulations were also given as dispersions in which 1 ml of oil containing 200 iu insulin was dispersed in 2 ml of warm phosphate saline before all three milliliters were administered i.j. to a single animal.

Sample Collection in Animals

The catheters used for collection of blood were flushed once daily with heparinised saline (500 iu/ml). On sampling days a less concentrated heparin solution (50 iu/ml) was used in the catheters between sampling.

At 09:00 on the study days a blood sample not exceeding 5 ml was taken, after withdraw 2 ml of blood to remove any residual anticoagulant from the catheter. The catheter was then flushed with 50 iu/ml heparin solution to prevent clotting in the cannula. The animal was then dosed according to the treatment schedule. Blood sampling and dosing was staggered to allow a number of animals to be handled at the same time. Blood samples, totalling 4 ml at each time point, were taken at 0.25., 0.5., 1.0., 1.5., 2.0., 3.0., 4.0., and 6.0. hours after dosing as for the 09:00 (time zero) samples.

Method of Assay

The blood samples were handled as follows:

After the discard, the first 2 ml was taken into a plastic heparinised container. The samples were then stored at +4° C. for up to 30 minutes before they were centrifuged in a refrigerated centrifuge at 3000 rpm for 20 minutes. The result plasma was then divided and transferred into two suitable containers and frozen to –20° C. prior to colorimetic assay of plasma calcium or glucaose concentrations using a Kone autoanalyser. One sample was assayed and the other retained.

RESULTS

Tables 1 and 2 below present the results of the animal studies in terms of AUC of fall in either calcium or glucose levels, as well as peak fall in calcium or glucose level.

TABLE 1

Results for Calcitonin formulations as described in Example 5

| Formulation details<br>Calcitonin administered at a dose of 5000 iu per animal | AUC of Ca fall<br>(4 hours) | Peak fall in Ca<br>mmol/L |
| --- | --- | --- |
| 1. sCT/aprotinin + Akoline/tween 80 mixture in PBS | −2.19 ± 0.97 | −0.74 ± 0.31 |
| 2. sCT/aprotinin + GDO/Tween 80 mixture in PBS | −0.6 ± 0.39 | −0.33 ± 0.26 |
| 3. sCT/aprotinin + Oleic acid/Tween 80 mixture in PBS | −0.5 ± 0.39 | −0.44 ± 0.04 |
| 4. sCT/aprotinin‖PC‖Akoline‖Tween 80 | −0.82 ± 0.89 | −0.39 ± 0.10 |
| 5. sCT/Aprotinin‖Cheno‖Akoline‖Tween 80 | −1.85 ± 1.48 | −0.63 ± 0.06 |
| 6. sCT/aprotinin‖Cheno‖oleic acid‖Tween 80 | −0.63 ± 0.38 | −0.24 ± 0.18 |
| 7. sCT‖Cheno‖Akoline‖Tween 80 | −1.73 ± 1.20 | −0.60 ± 0.36 |
| 8. sCT‖Urso‖Akoline‖Tween 80 | −2.26 ± 1.31 | −0.73 ± 0.44 |
| 9. sCT‖αTS‖Akoline‖Tween 80 | −2.22 ± 1.04 | −0.73 ± 0.32 |
| 10. sCT‖Docusate‖Akoline‖Tween 80 | −1.55 ± 0.83 | −0.54 ± 0.25 |

TABLE 2

Results for Insulin formulations as described in Example 6

| Formulation details<br>Insulin administered at a dose of 200 iu/animal | AUC of fall in glucose (4 hr) | Peak fall in glucose mmol/L |
|---|---|---|
| 11. Insulin/aprotinin + Akoline/Tween 80 mixture in PBS | −3.78 ± 2.65 | −2.34 ± 1.79 |
| 12. Insulin/aprotinin‖PC‖Akoline‖Tween 80 | −2.84 ± 2.97 | −1.45 ± 1.54 |
| 13. Insulin/aprotinin‖Cheno(high)‖Akoline‖Tween 80 | −2.02 ± 1.44 | −1.94 ± 1.17 |
| 14. Insulin/aprotinin‖Cheno(med)‖Akoline‖Tween 80 | −2.93 ± 1.58 | −1.96 ± 1.17 |
| 15. Insulin/aprotinin‖Cheno(low)‖Akoline‖Tween 80 | −2.98 ± 2.88 | −2.18 ± 1.68 |
| 16. Insulin/aprotinin‖Urso(low)‖Akoline‖Tween 80 | −3.66 ± 2.17 | −1.85 ± 1.29 |
| 17. Insulin alone‖Urso(low)‖Akoline‖Tween 80 | −5.69 ± 2.32 | −2.75 ± 0.59 |
| 18. Insulin/Urso in PBS | −2.09 ± 1.23 | −1.03 ± 0.93 |
| 19. Negative control (non Insulin) | −1.58 ± 1.03 | N/A |
| 11–18. | −1.69 | — |
| 17–18. | −3.60 | |

In Table 2, formulating insulin as a hydrophobic solution in medium-chain monoglyceride (17) gives a greater efficacy than a simple two-phase mixture of components(11). This is more noticeable in the AUC of fall of glucose, rather than the peak glucose fall, indicating that a longer duration of action is an important factor in improvement of efficacy. Subtraction of the AUC value of group (18) from (11) and(17) gives the contribution made by the delivery vehicle over and above the effect of insulin administered in free form. As can be seen, the insulin formulated as a solution in medium-chain monoglyceride gives over double the enhancement afforded by a simple mixture of the components.

What is claimed is:

1. A hydrophobic preparation comprising:
   (i) an oil phase comprising one or more medium chain monoglycerides and one or more medium chain diglycerides, said mono- and di-glycerides having chain lengths of 8 to 10 carbon atoms, said oil phase optionally comprising an additional compound selected from oleic acid, glycerol mono-oleate or a gelucire, wherein the monoglyceride(s) make(s) up 40–90% of the total amount of oil present;
   (ii) at least one amphiphile selected from the group consisting of phosphatidyl choline, phosphatidic acid, phosphatidyl glycerol, phosphatidyl ethanolamine, phosphatidyl serine or lyso derivatives thereof, octyl glucoside, tocopherol succinate, cholesterol hemisuccinate, sodium docusate, hydroxypropyl cellulose, and a bile salt, said bile salt being selected from the group of bile salts consisting of cholate, deoxycholate, chenodeoxycholate, ursodeoxycholate, taurocholate, taurodeoxycholate, tauroursodeoxycholate, taurochenodeoxycholate, glycholate, glycodeoxycholate, glycoursodeoxycholate, glycochenodeoxycholate, lithocholate, taurolithocholate and glycolithocholate; and
   (iii) a hydrophilic species solubilized or dispersed in the mixture of mono- and di-glycerides; wherein the hydrophilic species is not normally soluble in the mono- or di-glycerides and is selected from the group consisting of proteins, glycoproteins, nucleic acids analogues thereof and polysaccharides; said preparation containing no free water molecules.

2. A hydrophobic preparation as claimed in claim 1 wherein the oil phase comprises 60–70% medium chain monoglycerides.

3. A hydrophobic preparation as claimed in claim 1 wherein the ratio of amphiphile: hydrophilic species is in the range 1:1 to 20:1 by weight.

4. A hydrophobic preparation as claimed in claim 3 wherein the ratio of amphiphile: hydrophilic species 1, 2:1 to 8:1 by weight.

5. A hydrophobic preparation as claimed in claim 1 wherein the hydrophilic species is a protein.

6. A hydrophobic preparation as claimed in claim 5 wherein the protein is selected from the group consisting of insulin, calcitonin, haemoglobin, soy bean trypsin inhibitor, aprotinin, glucagon-like peptide 1, erythropoietin, somatotropin, growth honnone, growth hormone releasing factor, galanin, urokinase, blood factors, tissue plasminogen activator, superoxide dismutase, catalase, peroxidase, interferon, somatostatin, hirudin, leutinizing hormone releasing hormone and an analogue or fragment thereof.

7. A hydrophobic preparation as claimed in claim 1 which further comprises one or more further components selected from antioxidants, metal chelating agents, and dispersion agents.

8. An emulsion preparation comprising a hydrophobic preparation as defined in claim 1.

9. A pharmaceutical formulation comprising a hydrophobic preparation as defined in claim 1.

* * * * *